(12) United States Patent
Liu (10) Patent No.: US 10,674,766 B2
(45) Date of Patent: Jun. 9, 2020

(54) ATOMIZING ASSEMBLY AND ELECTRONIC CIGARETTE

(71) Applicant: HUIZHOU KIMREE TECHNOLOGY CO., LTD. SHENZHEN BRANCH, Huizhou, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 461 days.

(21) Appl. No.: 15/508,480

(22) PCT Filed: Sep. 2, 2014

(86) PCT No.: PCT/CN2014/085779
§ 371 (c)(1),
(2) Date: Mar. 2, 2017

(87) PCT Pub. No.: WO2016/033741
PCT Pub. Date: Mar. 10, 2016

(65) Prior Publication Data
US 2017/0273359 A1 Sep. 28, 2017

(51) Int. Cl.
*A24F 47/00* (2020.01)
*A61M 11/04* (2006.01)
*A61M 15/06* (2006.01)

(52) U.S. Cl.
CPC ......... *A24F 47/008* (2013.01); *A61M 11/042* (2014.02); *A61M 11/044* (2014.02); *A61M 15/06* (2013.01)

(58) Field of Classification Search
CPC .. A24F 13/00; A24F 13/16; A24F 9/16; A24F 47/008; A61M 11/041; A61M 11/044; A61M 15/06; A61M 11/042
See application file for complete search history.

(56) References Cited

U.S. PATENT DOCUMENTS

| | | | | |
|---|---|---|---|---|
| 2013/0319438 A1* | 12/2013 | Liu | ........................ | A24F 47/008 131/329 |
| 2014/0150783 A1* | 6/2014 | Liu | ........................ | A24F 47/008 128/202.21 |
| 2017/0013885 A1* | 1/2017 | Qiu | ........................ | A61M 11/042 |

* cited by examiner

*Primary Examiner* — Bradley H Philips
*Assistant Examiner* — Nathan M Le (57) ABSTRACT

The present application discloses an atomizing assembly and electronic cigarette. The atomizing assembly comprises a connecting assembly, an atomizing core, an oil cup assembly and a sealing gasket. The connecting assembly comprises a connecting base and a lower electrode. The oil cup assembly comprises an oil storage sleeve, a vent pipe, and a mounting sleeve which enclose to form an oil storage chamber for storing smoke oil. The connecting base and the oil storage sleeve are either abutted against or expandedly fitted with each other. The connecting base is cappingly provided on an oil filler of the oil storage sleeve. The atomizing core comprises an atomizing sleeve, a heating wire assembly, a smoke oil retention member and an inner electrode. The inner electrode is abutted against and electrically connected to the lower electrode. The atomizing core is slidably sleeved in the mounting sleeve.

20 Claims, 7 Drawing Sheets

ATOMIZING ASSEMBLY AND ELECTRONIC CIGARETTE

FIELD OF THE INVENTION

The present application relates to a field of electric heating products, and more particularly relates to an atomizing component and an electronic cigarette.

BACKGROUND OF THE INVENTION

In the prior arts, an electronic cigarette on the market comprise an atomization assembly for atomizing smoke liquid and a battery assembly for supplying power to the atomizing assembly. When the electronic cigarette is working, the battery assembly supplies power to an heat generating element in the atomizing assembly, so that the smoke liquid can be atomized to achieve an effect of producing smoke.

In the prior arts, the atomization assembly comprises an oil cup assembly, a connecting assembly, and an atomizing core, a connection between ends of the atomizing core and the connecting assembly is a fixed connection. Therefore, it is inconvenient to disassemble the atomizing core, and when replacing the atomizing core, the connecting assembly must be discarded together with the atomizing core, resulting in a higher cost of replacing the atomizing core.

SUMMARY OF THE INVENTION

Technical problems to be solved in the present invention is to provide an atomizing assembly and an electronic cigarette comprising an atomizing core having a convenient disassembly, a convenient and lower cost replacement.

Technical solutions of the present application for solving the technical problems are to provide an atomizing assembly for forming an electronic cigarette in combination with a battery assembly, the atomizing assembly comprises a connecting assembly, an atomizing core, an oil cup assembly and a sealing gasket, the sealing gasket is configured for preventing smoke oil from leaking along a gap between the oil cup assembly and the connecting assembly; the connecting assembly comprises a connecting base for detachably connecting the oil cup assembly and the battery assembly respectively, and a lower electrode for electrically connecting with the battery assembly; the oil cup assembly comprises an oil storage sleeve, a vent pipe, and a mounting sleeve; the vent pipe is located in the oil storage sleeve for discharging smoke produced by an atomization of the atomizing core, the mounting sleeve is configured for accommodating the atomizing core; the oil storage sleeve, the vent pipe and the mounting sleeve enclose an oil storage chamber for storing the smoke oil; the connecting base is abutted against or connected to the oil storage sleeve with interference fit, and the connecting base is provided on an oil filler of the oil storage sleeve; one end of the mounting sleeve is fixedly connected to the vent pipe, and the other end of the mounting sleeve is detachably connected to the connecting base by a thread or snap structure, the mounting sleeve is provided with a first oil guide hole communicating with the oil storage chamber; the atomizing core comprises an atomizing sleeve, a heating wire assembly, a smoke oil retention member and an inner electrode, and the smoke oil retention member is made of oil absorbing materials, the heating wire assembly is electrically connected to the inner electrode, the smoke oil retention member and the heating wire assembly are accommodated in the atomizing sleeve, the smoke oil retention member is configured for adsorbing smoke oil derived from the first oil guide hole for an atomization of the heating wire assembly, the inner electrode is located at one end of the atomizing sleeve, the inner electrode is abutted against and electrically connected to the lower electrode; the atomizing core is slidably sleeved in the mounting sleeve so as to remove the atomizing core after disassembling the connecting assembly.

In the atomizing component provided by the present invention, the lower electrode and the vent pipe clamp two ends of the atomizing core to fix the atomizing core.

In the atomizing component provided by the present invention, the sealing gasket is located between the oil cup assembly and the connecting assembly, and the sealing gasket is provided with an annular sealing groove, the oil storage sleeve is inserted in the sealing groove.

In the atomizing component provided by the present invention, a limit protrusion for restricting the sealing gasket is formed along a circumferential direction of the connecting base; the sealing gasket is defined outside the mounting sleeve and an outer wall surface of the sealing gasket is abutted against the limit protrusion so that the sealing gasket seals and covers on the oil filler of the oil storage sleeve.

In the atomizing component provided by the present invention, the first oil guide hole serving as an oil guide passage is provided on a side wall of the mounting sleeve, the atomizing sleeve is provided with a second oil guide hole communicated with the first oil guide hole for smoke oil in the oil storage chamber to flow into the atomizing core; the smoke oil retention member is inserted into the atomizing sleeve and is fitted to an inner peripheral surface of the atomizing sleeve, the smoke oil retention member is configured for storing smoke oil passing through the first oil guide hole and the second oil guide hole to flow into the atomizing core, and supplying the smoke oil to the heating wire assembly for an atomization.

In the atomizing component provided by the present invention, the connecting base has a connecting through hole extending through the connecting base, one end of the connecting through hole is provided with a first connecting sleeve, the end is near the vent pipe, the mounting sleeve is provided with a threaded structure which mates with the first connecting sleeve, the lower electrode is inserted in the connecting through hole.

In the atomizing component provided by the present invention, an outer wall surface of the first connecting sleeve is in interference with an inner wall surface of the connecting through hole.

In the atomizing component provided by the present invention, the heating wire assembly comprises an oil guide connected to the smoke oil retention member and a heating wire, the heating wire is wound around the oil guide, the oil guide is configured for transferring the smoke oil obtained from the smoke oil retention member to the heating wire for heating and atomizing.

In the atomizing component provided by the present invention, the heating wire assembly further comprises a fiberglass tube inserted in the smoke oil retention member, the fiberglass tube is provided with a mounting hole through which the oil guide passes, the heating wire is wound around the oil guide located in the fiberglass tube.

In the atomizing component provided by the present invention, the atomizing assembly further comprises a suction nozzle assembly detachably connected to the oil cup assembly, the suction nozzle assembly having a smoke passage extending through the suction nozzle assembly, the smoke passage is communicated with the vent pipe for smoke obtained from the atomization to pass through.

In the atomizing component provided by the present invention, the suction nozzle assembly comprises a suction nozzle for sucking smoke by users, a suction nozzle connection sleeve and a second connection sleeve, one end of the suction nozzle connection sleeve is detachably connected to or integrally formed with the suction nozzle, and the other end of the suction nozzle connection sleeve is detachably connected to or integrally formed with the second connection sleeve.

In the atomizing component provided by the present invention, the suction nozzle connection sleeve is detachably connected to the second connection sleeve, an end surface of the suction nozzle connection sleeve extending outwardly to form an inner sleeve, the end surface is close to the oil cup assembly, one end of the second connection sleeve is inserted into the inner sleeve, and the other end of the second connection sleeve is detachably connected to the oil storage sleeve.

In the atomizing component provided by the present invention, the atomizing assembly further comprises a sealing ring for preventing smoke oil from flowing out of the oil storage chamber along the gap between the connecting assembly and the oil cup assembly.

In the atomizing component provided by the present invention, the end surface of the suction nozzle connecting sleeve is also provided with an outer sleeve pipe which is sheathed outside the inner sleeve; the sealing ring is interposed between the inner sleeve and the outer sleeve pipe, and an end surface of the oil storage sleeve is abutted against the sealing ring.

In the atomizing component provided by the present invention, the suction nozzle connection sleeve is detachably connected to the suction nozzle, an end surface of the suction nozzle connection sleeve extending outwardly to form a nozzle fixed sleeve, the end surface is close to the suction nozzle, the suction nozzle is inserted into the nozzle fixed sleeve.

In the atomizing component provided by the present invention, the atomizing core further comprises an atomizing cap defined at one end of the atomizing sleeve, the end is opposite to the inner electrode, the atomizing cap is provided with an atomizing cap through hole penetrating through the atomizing cap, and the atomizing cap through hole is communicated with the vent pipe.

In the atomizing component provided by the present invention, the connecting base and the atomizing sleeve are made of a conductive material or a conductive layer is defined on a surface of the connecting base and the atomizing sleeve, when the battery assembly supplies power to the atomizing assembly, the connecting base is electrically connected to the battery assembly and the atomizing sleeve, respectively, the lower electrode is electrically connected to the battery assembly and the inner electrode, respectively; a first insulation sleeve is defined between the connecting base and the lower electrode, the first insulation sleeve electrically isolates the connecting base from the lower electrode; a second insulation sleeve is defined between the atomizing sleeve and the inner electrode, and the second insulation sleeve makes the atomizing sleeve be electrically isolated with the inner electrode.

In the atomizing component provided by the present invention, an end surface of the inner electrode is provided with a magnetic member magnetically connected to the connecting assembly so as to suck out the atomizing core when the connecting assembly is removed; the end surface is abutted against the lower electrode.

In the atomizing component provided by the present invention, the atomizing core further comprises an atomizing cap and an elastic member; the atomizing cap is provided at one end of the atomizing sleeve, the end is opposite to the inner electrode; the elastic member is defined between the vent pipe and the atomizing cap, the atomizing core is resiliently abutted against the vent pipe through the elastic member.

The present invention further comprises an electronic cigarette, the electronic cigarette comprises the atomizing assembly and the battery assembly in the above, the battery assembly is configured for supplying electrical power to the atomizing assembly.

Applications of the atomizing component and an electronic cigarette of the present invention have following advantages:

(1) The atomizing core in the present invention is not fixedly connected to the connecting assembly as in the prior arts, but is fixed at two ends in a clamped manner and slidably fitted in the mounting sleeve. When the user needs to remove the atomizing core, they only need to simply remove the oil cup assembly from the connecting assembly, and then slide the atomizing core out, and remove the atomizing core without twisting or touching the atomizing core, so as to well avoid smoke oil pollution and to avoid a need for other auxiliary tools, it not only simplifies steps of disassembly of the atomizing core, but also significantly reduces time spent on a disassembly process, besides, the smoke oil can be well sealed through the clamped manner at the two ends, so as to prevent the atomizing core connected in manners of a thread and other connections from easily producing issues of leaking the smoke oil from the lines, an easy dislocation, and so on.

(2) Since the connecting base is abutted against or interference fitted with the oil storage chamber sleeve, and the connecting base is provided on the oil filler of the oil storage sleeve, it is only necessary to remove the connecting assembly when adding the smoke oil, then it is possible to avoid problems of an unstable electrical connection and the leakage of the smoke oil caused by a lose connection between the connection structures resulted by a frequent disassembly of the atomizing core.

(3) Two ends of the atomizing core are abutted against the oil cup assembly and the lower electrode, respectively, and are clamped by the oil cup assembly and the lower electrode. This fixing method can play a cushioning effect, enhance a seismic capacity of the atomizing core, seal the smoke oil to prevent the smoke oil leakage well.

(4) Since the sealing gasket is provided outside the mounting sleeve and the outer wall surface of the sealing gasket is in abutment with the limit protrusion, the sealing gasket seals and covers on the oil filler of the oil storage sleeve, thereby preventing the smoke oil from leaking out from a gap among the connecting assembly, the oil storage sleeve and the mounting sleeve.

(5) The inner electrode is provided with a magnetic member on the end face which is abutted against the lower electrode so as to remove the atomizing core from the mounting sleeve conveniently.

(6) The elastic member is provided between the vent pipe and the atomizing cap so as to remove the atomizing core from the mounting sleeve conveniently; meanwhile, the atomizing core is further clamped to ensure a reliable electrical connection between the inner electrode and the lower electrode when the coupling assembly is tightened with the oil cup assembly; in addition, it can also play a buffer role, enhance the seismic capacity of the atomizing core.

BRIEF DESCRIPTION OF THE DRAWINGS

The present invention will be further described with reference to the accompanying drawings and embodiments in the following.

DETAILED DESCRIPTION OF THE PREFERRED EMBODIMENT

To make the technical feature, objective and effect of the present application be understood more clearly, now the specific implementation of the present application is described in detail with reference to the accompanying drawings and embodiments.

The present invention provides an atomizing assembly configured for combining with a battery assembly (not shown) to form electronic cigarette, the battery assembly includes a battery for supplying power to the atomizing assembly, a control circuit board for controlling an operating state of the atomizing assembly, battery electrodes for electrically connecting to the atomization assembly, and a battery case for accommodating the battery, the control circuit board and the battery electrodes. Since related structures and arrangements of the battery assembly in the present invention belong to the prior arts, they will not be described here.

Figure 1:
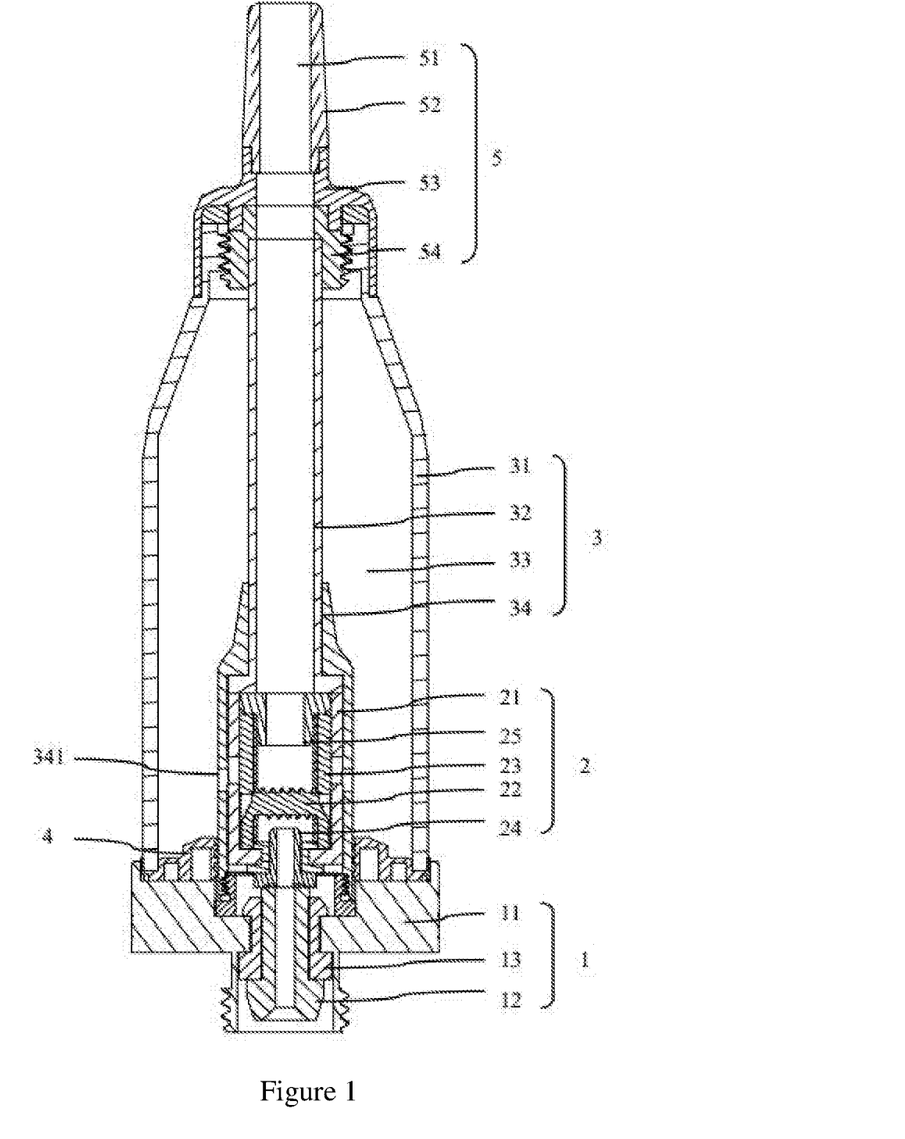
FIG. 1 is a schematic structural view of an atomizing assembly of an electronic cigarette provided in the first preferred embodiment of the present invention.

First embodiment: referring to FIG. 1 combining with FIG. 2, FIG. 3, FIG. 4, FIG. 5 and FIG. 6.

Figure 2:
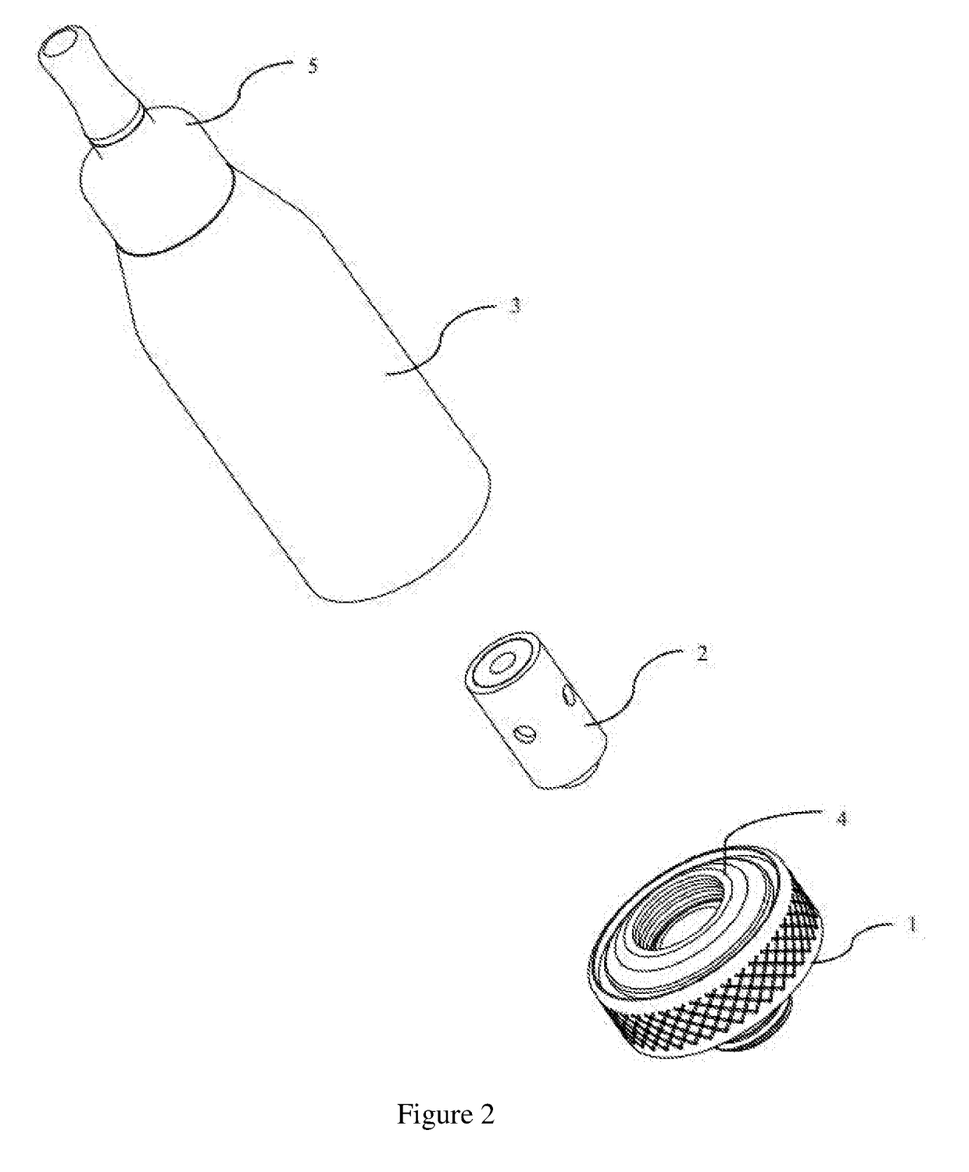
FIG. 2 is a three-dimensional split diagram of the atomization assembly of the electronic cigarette in FIG. 1.

The atomizing assembly comprises a connecting assembly 1, an atomizing core 2, an oil cup assembly 3, a sealing gasket 4 and a suction nozzle component 5, the connecting assembly 1 is detachably connected to the oil cup assembly 3, the sealing gasket 4 and the battery assembly, respectively; and two ends of the atomizing core 2 are abutted against the connecting assembly 1 and the oil cup assembly 3, respectively.

The connecting assembly 1 comprises a connecting base 11 for detachably connecting to the oil cup assembly 3 and the battery assembly respectively, a lower electrode 12 for electrically connecting with the battery assembly, and a first insulation sleeve 13 for electrically isolating the connecting base 11 from the lower electrode 12.

Figure 3:
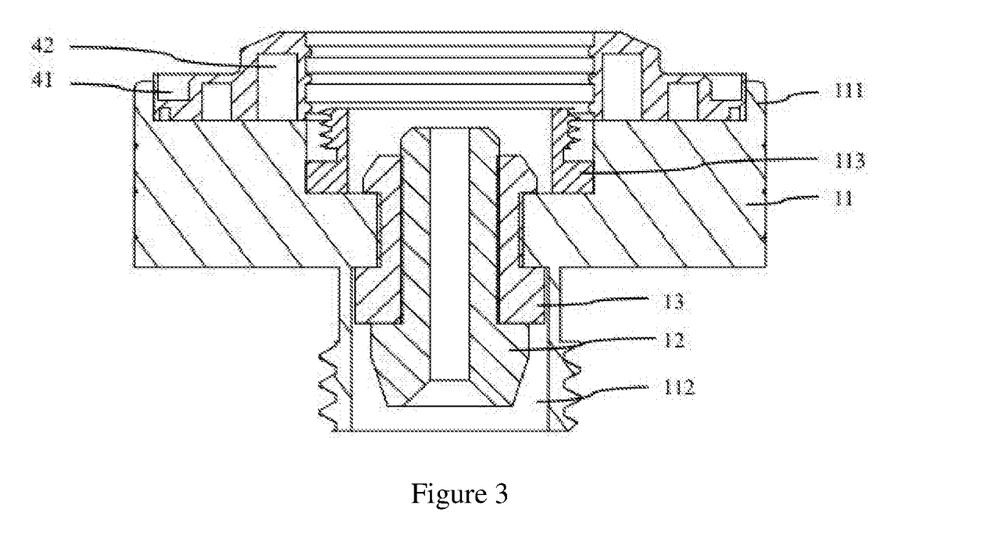
FIG. 3 is a cross-sectional view of a connecting assembly of FIG. 1.

With reference to FIG. 3, the connecting base 11 is made of a conductive material or a conductive layer is defined on a surface of the connecting base 11, so that the connecting base 11 can be directly used as electrodes to electrically connect to the battery assembly and the atomizing core 2, respectively, the first insulation sleeve 13 is clamped between the connecting base 11 and the lower electrode 12 to ensure that the connecting base 11 is electrically isolated from the lower electrode 12.

The connecting base 11 has a connecting through hole 112 extending through the connecting base 11, and the first connecting sleeve 113 inserted in one end of the connecting through hole 112 near the oil cup assembly 3, the connecting through hole 112 is shaped in steps along an axial direction of the connecting through hole 112, the lower electrode 12 and the first insulation sleeve 13 are inserted into the connecting through hole 112 and the lower electrode 12 is configured for abutting against the electrodes in the battery assembly to achieve an electrical connection the first connecting sleeve 113 is a stepped sleeve, a portion of the first connecting sleeve 113 having a larger diameter is fixedly connected to the connecting through holes 112 by an interference fit, so that the first connecting sleeve 113 is prevented from falling out of the connecting through hole 112; a portion of the first connecting sleeve 113 having a small diameter is provided with a threaded structure for a detachable connection to the oil cup assembly 3.

It is to be understood that the connecting base 11 may also be an integrally formed structure.

Figure 6:
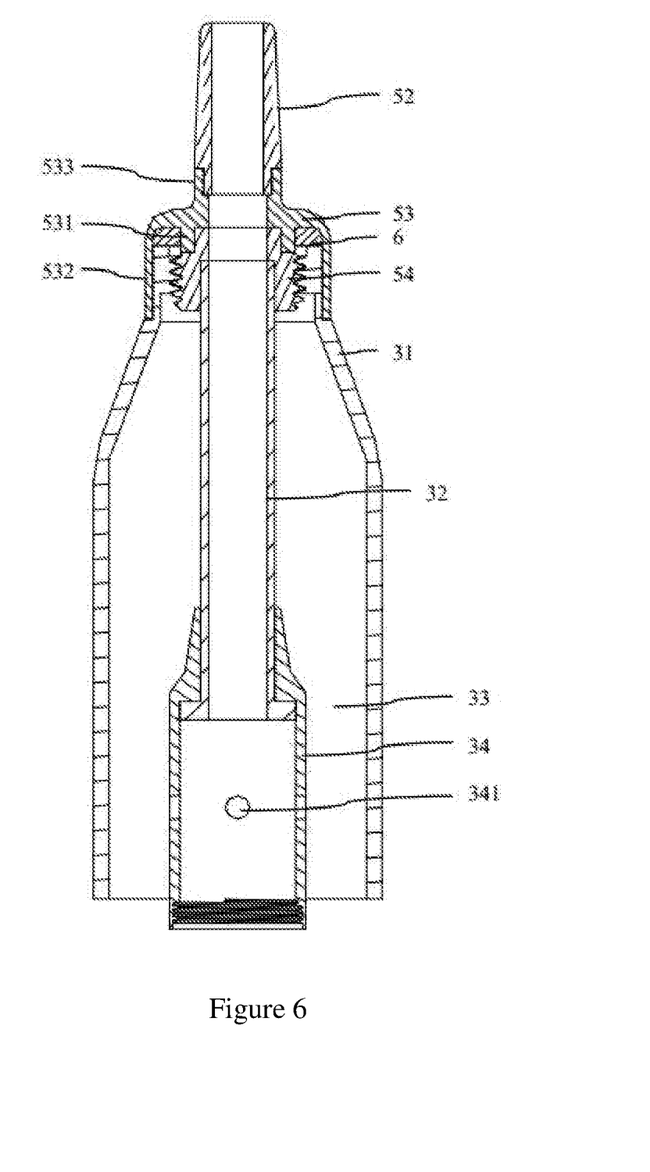
FIG. 6 is a cross-sectional view of the oil cup assembly of FIG. 1.

Referring to FIG. 6 with FIG. 1, the oil cup assembly 3 comprises an oil storage sleeve 31, a vent pipe 32, and a mounting sleeve 34; the vent pipe 32 is located in the oil storage sleeve 31 for discharging smoke produced by an atomization of the atomizing core 2, the mounting sleeve 34 is configured for accommodating the atomizing core 2; the oil storage sleeve 31, the vent pipe 32 and the mounting sleeve 34 enclose an oil storage chamber 33 for storing the smoke oil.

The connecting base 11 completely covers on an oil filler of the oil storage sleeve 31 to avoid the leakage of the smoke oil, and the connecting base 11 is abutted against or connected to the oil storage sleeve 31 with interference fit. In the present embodiment, in order to enhance sealing capability between the connecting base 11 and the oil storage sleeve 31, the sealing gasket 4 is added between the two.

Preferably, the oil storage sleeve 31 is a transparent body made of a material like plastics, thus the remaining amount of the smoke oil in the oil storage chamber 33 can be well observed, so that new smoke oil can be added in a timely manner when the smoke oil is exhausted.

The vent pipe 32 is of a hollow tubular structure to form an airflow channel for smoke to flow through; preferably, the vent pipe 32 is axially disposed along the atomization assembly. One end of the vent pipe 32 is inserted into the suction nozzle assembly 5, and the other end is inserted into the mounting sleeve 34, the vent pipe 32 are respectively connected with the suction nozzle assembly 5 and the mounting sleeve 34 by a interference fit manner to achieve a fixed connection.

It is to be understood that manners for a connection between the vent pipe and the suction nozzle assembly 5 and a connection between the vent pipe and the mounting sleeve 34 may also be thread connections, snap fit connections or other connections, which are not limited here.

The mounting sleeve 34 is configured for accommodating the atomizing core 2, one end of the mounting sleeve 34 is sleeved on the end of the vent pipe 32, while the other end is detachably connected to the first connecting sleeve 113 of the connecting base 11 by a threaded or snap-fit structure. The mounting sleeve 34 and the first connecting sleeve 113 are respectively provided with mating threaded structures, so that the connecting base 11 and the oil cup assembly 3 can be detachably connected.

It is to be understood that the detachable connection between the mounting sleeve 34 and the first connecting sleeve 113 may be other means such as an engagement connection, and is not particularly limited thereto.

In the present embodiment, the lower electrode 12 and the vent pipe 32 respectively clamp the atomizing core 2 from two ends to fix the atomizing core 2, it will be appreciated that, when a portion of the vent pipe 32 extending into the mounting sleeve 34 is short, the two ends of the atomizing core 2 can be respectively abutted against the lower electrode 12 and the mounting sleeve 34 as well, as long as it can ensure that the oil cup assembly 3 and the lower electrode 12 clamp and fix the atomizing core 2 from the two ends, this is not specifically limited here.

Preferably, an outer wall surface of the atomizing core 2 is attached to an inner wall surface of the mounting sleeve 34, so as to prevent the atomizing core 2 shaking in the mounting sleeve 34 that resulting in an unstable connection between an inner electrode 24 in the atomizing core 2 and the lower electrode 12.

Preferably, when there is a gap between the outer wall surface of the atomizing core 2 and the inner wall surface of the mounting sleeve 34, in order to ensure a stable electrical connection between the inner electrode 24 and the lower electrode 12, a buffer structure such as a silicone sleeve may be provided between the atomizing core 2 and the mounting sleeve 34, and is not specifically limited thereto.

The sealing gasket 4 serves to prevent the smoke oil from flowing out of the oil storage chamber 33 along the gap between the oil cup assembly 3 and the connecting assembly 1. In this embodiment, the sealing gasket 4 is provided outside the mounting sleeve 34 and the sealing gasket 4 is provided with an annular sealing groove 41, the end of the oil storage sleeve 31 is inserted and clamped into the sealing groove 41.

The oil cup assembly 3 and the connecting assembly 1 are screwed through the screw structures between the vent pipe 32 and the first connecting sleeve 113 so that the end portion of the oil storage sleeve 31 is further pressed against the sealing gasket 4 after being inserted into the sealing groove 41 to achieve a seal.

A limit protrusion 111 for restricting the sealing gasket 4 is protruded to form along a circumferential direction of the connecting base 11; an outer wall surface of the sealing gasket 4 is abutted against the limit protrusion 111 so that the sealing gasket 4 seals and covers on the oil filler of the oil storage sleeve 31. When the oil cup assembly 3 and the connecting assembly 1 are tightened, the oil storage sleeve 31 presses the sealing gasket 4 and presses the sealing gasket 4 to be deformed under the restriction of the mounting sleeve 34 and the limit protrusion 111 to sufficiently fill the gap between the oil cup assembly 3 and the connecting assembly 1 to further enhance the sealing effect of the sealing gasket 4.

Preferably, the limit protrusion 111 is integrally formed with the connecting base 11 and the outer wall surfaces of the two are smoothly connected.

It is preferable that the sealing gasket 4 is provided with at least one deformation groove 42 on the end surface close to the connecting base 11 for increasing softness and deformationability of the sealing gasket 4 so as to further enhance the sealing effect of the sealing gasket 4.

The atomizing core 2 is slidably fitted in the mounting sleeve 34 so as to remove the atomizing core 2 after disassembling the connecting assembly 1, two ends of the atomizing core 2 are clamped by the lower electrode 12 and the vent pipe 32. The atomizing core 2 in the present invention is not fixedly connected to the connecting assembly 1 as in the prior arts, but is fixed by corporation among the mounting sleeve 34, the lower electrode 12 and the vent pipe 32. The atomizing core 2 can be slidable in the mounting sleeve 34. When the user needs to remove the atomizing core 2, they only need to simply remove the oil cup assembly 3 from the connecting assembly 1, and then slide the atomizing core 2 out from the mounting sleeve 34, and remove the atomizing core 2 without twisting or touching the atomizing core 2, so as to well avoid smoke oil pollution and to avoid a need for other auxiliary tools, it not only simplifies steps of disassembly of the atomizing core, but also significantly reduces time spent on a disassembly process, besides, the smoke oil can be well sealed through the clamped manner at the two ends, so as to prevent the atomizing core connected in manners of a thread and other connections from easily producing issues of leaking the smoke oil from the lines, an easy dislocation, and so on.

In addition, the connecting base 11 and the sealing gasket 4 both cover on the oil filler of the oil storage sleeve 31, thus it is only necessary to remove the connecting assembly when adding the smoke oil and there is no need to disassemble the atomizing core, then it is possible to avoid problems of an unstable electrical connection and the leakage of the smoke oil caused by a lose connection between the connection structures resulted by a frequent disassembly of the atomizing core.

Figure 4:
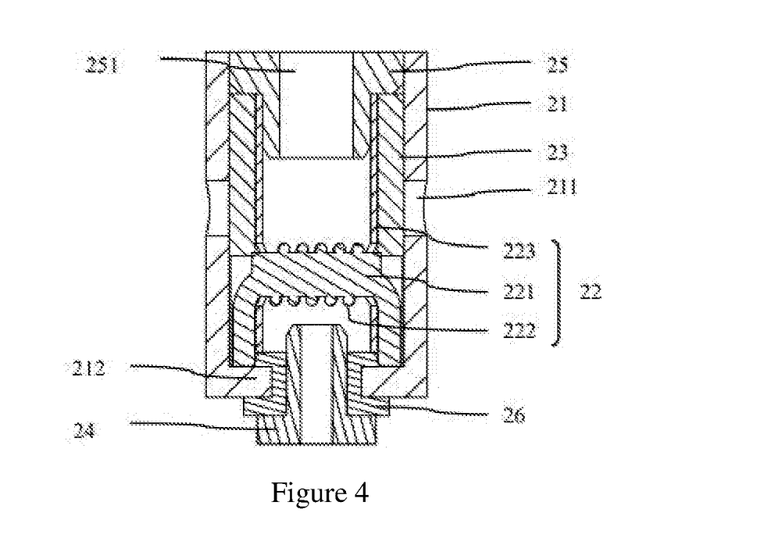
FIG. 4 is a cross-sectional view of an atomizing core of FIG. 1.
Figure 5:
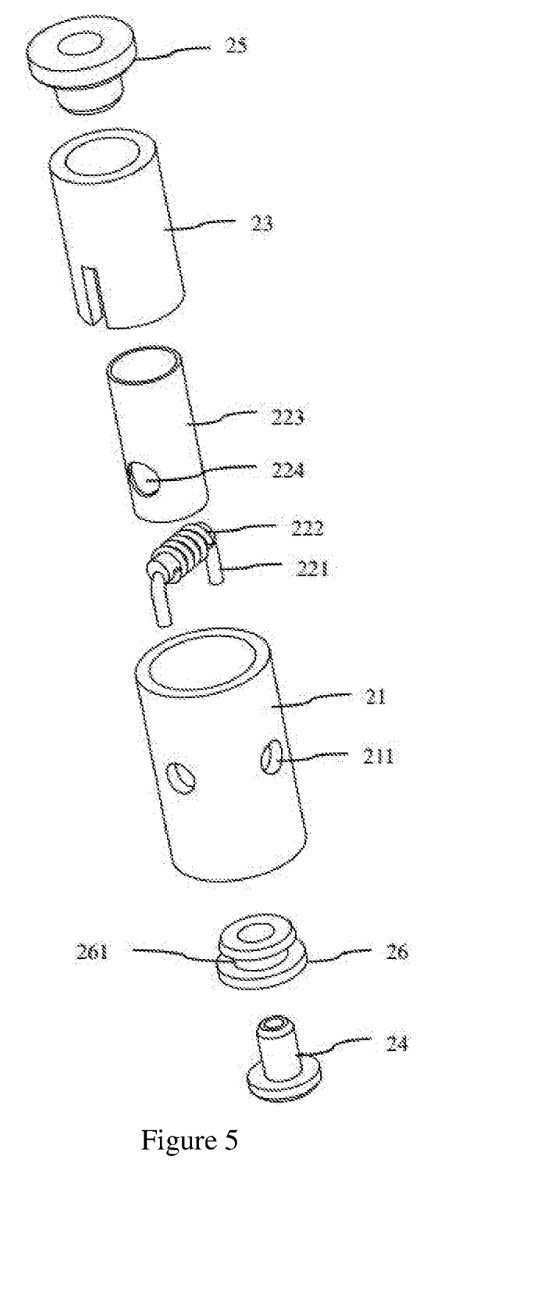
FIG. 5 is a three-dimensional split diagram of the atomizing core of FIG. 1.

With reference to FIG. 4 and FIG. 5, the atomizing core 2 comprises an atomizing sleeve 21, a heating wire assembly 22, a smoke oil retention member 23 made of an oil absorbing material, the inner electrode 24, an atomizing cap 25, and a second insulation sleeve 26.

The heating wire assembly 22 and the smoke oil retention member 23 are accommodated in the atomizing sleeve 21, the inner electrode 24 and the atomizing cap 25 are respectively located at the two ends of the atomizing sleeve 21, the inner electrode 24 is electrically connected to the heating wire assembly 22 and the lower electrode 12, respectively, the inner electrode 24 is abutted against the lower electrode 12, the atomizing cap 25 is abutted against the vent pipe 32 so that the vent pipe 32 is firmly received in the atomizing sleeve 21. Certainly, It is not necessary to provide the atomizing cap 25 as well, and this is not particularly limited thereto.

Preferably, an additional sealing structure such as a sealing gasket may be provided between the atomizing cap 25 and the vent pipe 32 to prevent the smoke produced by an atomization from leaking.

The atomizing sleeve 21 is made of a conductive material or a conductive layer is defined on a surface of the atomizing sleeve 21, so that the atomizing sleeve 21 can be served as the electrodes to electrically connect to the connecting assembly 1 and the heating wire assembly 22, respectively. Therefore, the second insulation sleeve 26 interposed between the atomizing sleeve 21 and the inner electrode 24 electrically isolates the atomizing sleeve 21 from the inner electrode 24.

An inner peripheral surface of the atomizing sleeve 21 protrudes inwardly to form a fixing table 212, and the second insulation sleeve 26 is provided with a fixing groove 261 (shown in FIG. 5) for engaging with the fixing table 212, the second insulation sleeve 26 is inserted in the atomizing sleeve 21, and the inner electrode 24 is inserted in the second insulation sleeve 26.

When the battery assembly supplies power to the atomizing assembly, the connecting base 11 is electrically connected to the battery assembly and the atomizing sleeve 21, respectively; the lower electrode 12 is electrically connected to the battery assembly and the inner electrode 24, respectively; the atomizing sleeve 21 and the inner electrode 24 are electrically connected to the heating wire assembly 22, respectively.

In order to ensure that the smoke oil in the oil storage chamber 33 can smoothly enter the heating wire assembly 22 in the atomizing core 2 for an atomization, the mounting sleeve 34 is provided with a first oil guide hole 341 communicating with the oil storage chamber 33, the atomizing sleeve 21 is correspondingly provided with a second oil guide hole 211 communicating with the first oil guide hole 341.

The heating wire assembly 22 comprises an oil guide 221 being abutted against the smoke oil retention member 23, a heating wire 222 and a fiberglass tube 223. The heating wire 222 is wound around the oil guide 221. The oil guide 221 is made of oil absorption materials and configured for transferring the smoke oil obtained from the smoke oil retention member 23 to the heating wire 222 for heating and atomizing; the fiberglass tube 223 is located in the atomizing sleeve 21 and is provided with a mounting hole 224 through which the oil guide 221 passes, the heating wire 222 is wound around a part of the oil guide 221 located in the fiberglass tube 223.

The smoke oil retention member 23 is preferably made of an oil absorbing material such as a nonwoven fabric or an oil storage sheet, and the smoke oil retention member 23 is sleeved in the atomizing sleeve 21 and fitted to the inner peripheral surface of the atomizing sleeve 21; meanwhile, the smoke oil retention member 23 completely covers the second oil guide hole 211 to prevent the smoke oil from flowing into the atomization casing 21 excessively through the second oil guide hole 211. In the present embodiment, the smoke oil in the oil storage chamber 33 penetrates the smoke oil retention member 23 through the second oil guide hole 211 and is then transferred by the smoke oil retention member 23 to the oil guide 221 connected to the smoke oil retention member 23, so as to be atomized by the heating wire 222.

The atomizing cap 25 is defined at one end of the atomizing sleeve 21, the end is close to the vent pipe 32, the atomizing cap 25 is provided with an atomizing cap through hole 251 penetrating through the atomizing cap 25, and the atomizing cap through hole 251 is communicated with the atomizing sleeve 21 and the vent pipe 32.

With reference to FIG. 6, the suction nozzle assembly 5 is detachably connected to the oil cup assembly 3, the suction nozzle assembly 5 has a smoke passage 51 penetrating through itself and the smoke passage 51 communicates with the vent pipe 32 for the smoke produced by the atomization to pass through.

The suction nozzle assembly 5 comprises a suction nozzle 52 for sucking smoke by users, a suction nozzle connection sleeve 53 and a second connection sleeve 54, two ends of the suction nozzle connection sleeve 53 are detachably connected to the suction nozzle 52 and the second connection sleeve 54, respectively.

It will be appreciated that the suction nozzle assembly 5 itself may also be a one-piece forming structure In the present invention, two ends of the suction nozzle connection sleeve 53 are detachably connected to the suction nozzle 52 and the second connection sleeve 54, respectively. An end surface of the suction nozzle connection sleeve 53 extending outwardly to form an inner sleeve 531 and an outer sleeve pipe 532, the end surface is close to the oil cup assembly 3 and the outer sleeve pipe 532 is sheathed outside the inner sleeve 531; an end surface of the suction nozzle connection sleeve 53 extending outwardly to form a nozzle fixed sleeve 533 for fixing the suction nozzle 52, the end surface is opposite to the oil cup assembly 3.

One end of the second connection sleeve 54 is inserted into the inner sleeve 531, and the other end thereof is provided with a screw structure for detachably connecting with the oil storage chamber 31. The second connection sleeve 54 and the inner sleeve 531 are fixedly connected by an interference fit.

It is to be understood that the detachable connection between the second connection sleeve 54 and the oil storage sleeve 31 is not limited to the screw connection in the present embodiment, but may be other means such as the engagement connection, the interference fit, and the like. The connection between the second connection sleeve 54 and the inner sleeve 531 is not limited to the interference fit connection in the present embodiment, and may be a screw connection, a snap connection, etc.

Preferably, a sealing ring 6 is further provided between the inner sleeve 531 and the outer sleeve pipe 532 for preventing the oil from flowing out of the oil storage chamber 33 through the gap between the suction nozzle assembly 5 and the oil cup assembly 3. The end surface of the oil storage sleeve 31 is abutted against the sealing ring 6 so that the inner wall surface of the sealing ring 6 is abutted against the second connection sleeve 54, and the sealing ring 6 is press-deformed so that the outer wall surface of the sealing ring 6 is tightly abutted against the inner wall surface of the suction nozzle connection sleeve 53 to seal.

The suction nozzle connection sleeve 53 is wrapped around the connection portion between the oil storage sleeve 31 and the second connection sleeve 54, and the oil storage sleeve 31 is clamped in a space between the outer sleeve pipe 532 and the second connection sleeve 54 to prevent oil storage sleeve 31 from loose.

Preferably, one end of the oil storage sleeve 31 near the suction nozzle assembly 5 is provided with a recess, the thickness of the oil storage sleeve 31 at the notch is adapted to the thickness of the suction nozzle connection sleeve 53, when the oil cup assembly 3 and the suction nozzle assembly 5 are tightened by the screw structure between the second connection sleeve 54 and the oil storage chamber 31, the outer peripheral surface of the electronic cigarette is flat and beautiful. The second connection sleeve 54 made of a metallic material enhances a reliability when it is threadedly connected to the oil storage sleeve 31 and improves the service life of the electronic cigarette.

The suction nozzle 52 can be used for the users to inhale the smoke produced by the atomization while the oil storage chamber 33 in the oil cup assembly 3 can be used to store the smoke oil. This arrangement can shorten a length of the electronic cigarette and facilitate the carrying of the users. It is only necessary to remove the connecting assembly 1 after an exhaust of the smoke oil, and the use time of the electronic cigarette can be increased by adding the smoke oil to the oil storage chamber 33.

It is to be understood that the oil cup assembly 3 and the suction nozzle assembly 5 in the present embodiment may also be an integral molding structure.

Figure 7:
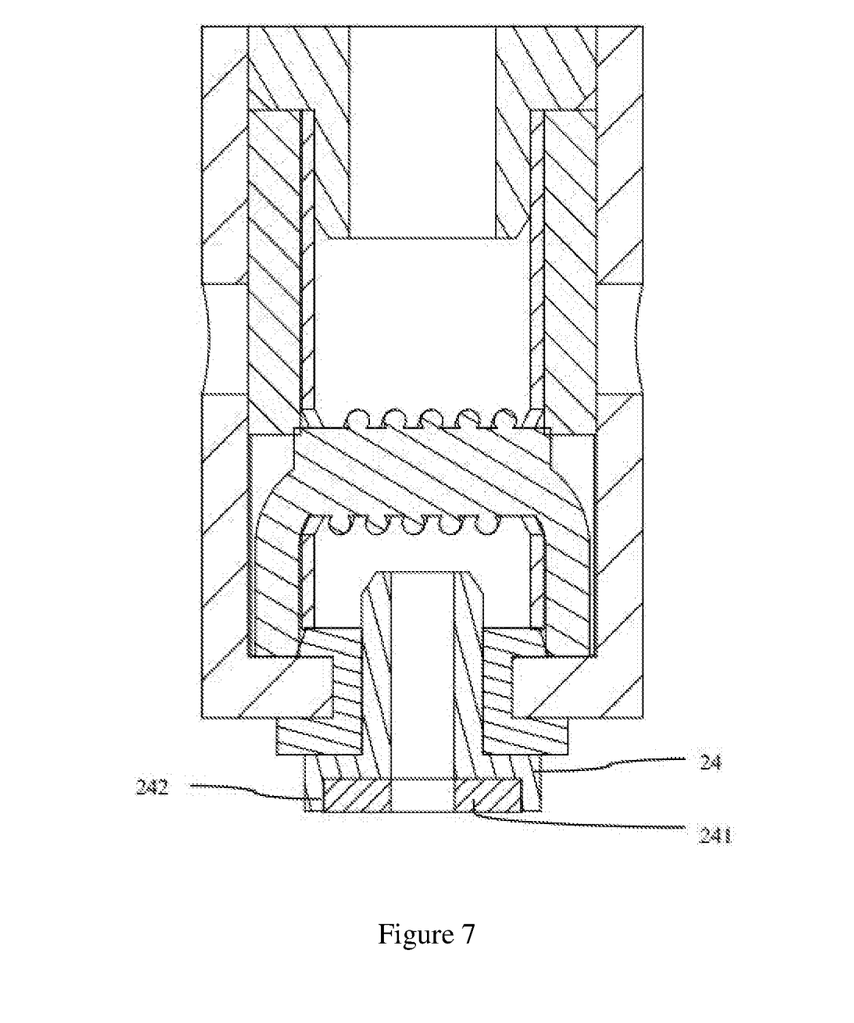
FIG. 7 is a schematic structural view of an atomizing core of an electronic cigarette provided in the second preferred embodiment of the present invention.

Second embodiment: referring to FIG. 7, in combination with FIG. 1.

Differences between the present embodiment and the first embodiment is that an end surface of the inner electrode 24 is provided with a magnetic member 241 magnetically connected to the connecting assembly 1 so as to suck out the atomizing core 2 from the mounting sleeve 34 when the connecting assembly 1 is removed; the end surface is abutted against the lower electrode 12. The inner electrode 24 is provided with a connecting groove 242 for accommodating the magnetic member 241.

It is preferable that the other magnetic member is embedded in the corresponding end surface of the lower electrode 12 and a magnetic attraction force between the inner electrode 24 and the lower electrode 12 ensures a reliable electrical connection between the inner electrode 24 and the lower electrode 12.

Figure 8:
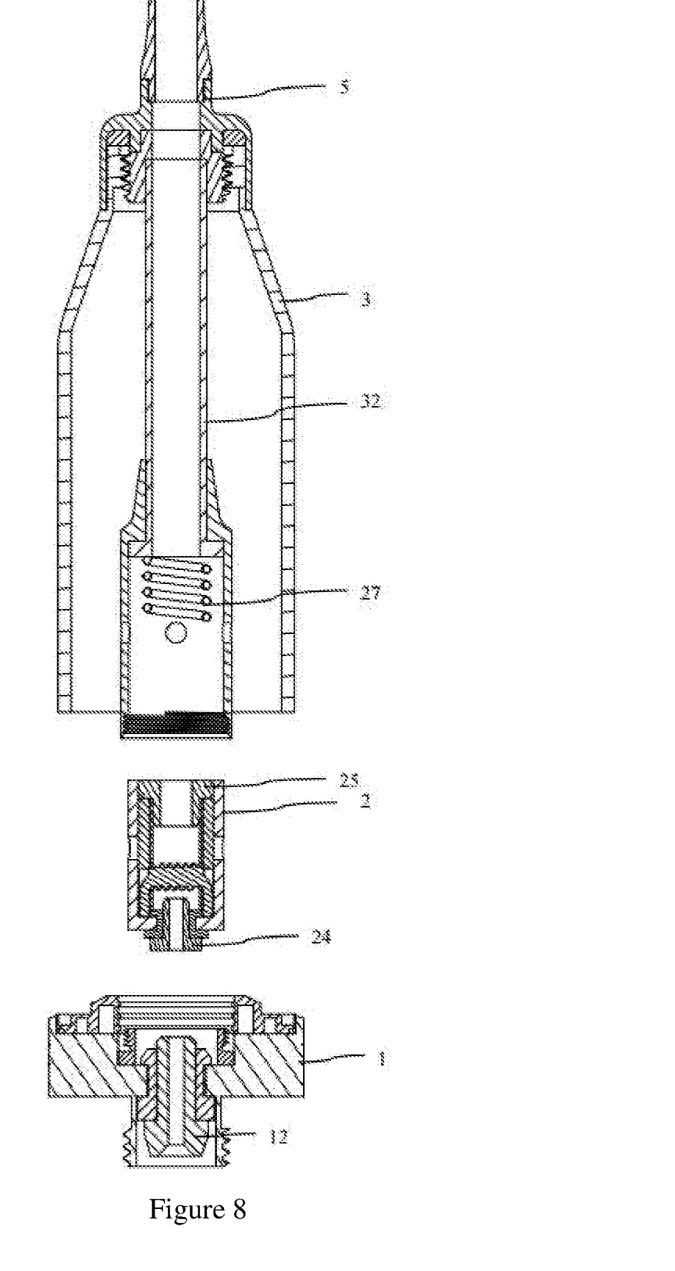
FIG. 8 a schematic structural view of an atomizing assembly of an electronic cigarette provided in the third preferred embodiment of the present invention.

Third embodiment refers to FIG. 8, in combination with FIG. 1.

Differences between the present embodiment and the first embodiment is that the atomizing core 2 further comprises an elastic member 27 defined between the vent pipe 32 and the atomizing cap 25, the atomizing core 2 is resiliently abutted against the vent pipe 32 through the elastic member 27.

When the connecting assembly 1 and the oil cup assembly 3 are disassembled, the elastic member 27 can eject the atomizing core 2 so as to take out the atomizing core 2. Meanwhile, when the connecting assembly 1 is screwed together with the oil cup assembly 3, the atomizing core 2 can be further pressed by the elastic member 27 to ensure a reliable electrical connection between the inner electrode 24 and the lower electrode 12 and to act as a cushioning force to enhance the seismic capacity of the atomizing core 2

When the connecting assembly 1 is tightened with the oil cup assembly 3, the elastic member 27 is maintained in a compressed state to ensure that the lower electrode 12 is tightly abutted against the inner electrode 24, so as to ensure that the atomizing core 2 can be clamped and fixed.

The elastic member 27 may be a spring, a resilient rubber pad, and the like.

Each embodiment of the present specification is described in a progressive manner, each embodiment is focused on the differences from other embodiments, and the same or similar parts between the various embodiments may be referred to each other.

While the embodiments of the present application are described with reference to the accompanying drawings above, the present application is not limited to the above-mentioned specific implementations. In fact, the above-mentioned specific implementations are intended to be exemplary not to be limiting. In the inspiration of the present application, those ordinary skills in the art can also make many modifications without breaking away from the subject of the present application and the protection scope of the claims. All these modifications belong to the protection of the present application.

The invention claimed is:

1. An atomizing assembly for forming an electronic cigarette in combination with a battery assembly, wherein the atomizing assembly comprises a connecting assembly (1), an atomizing core (2), an oil cup assembly (3) and a sealing gasket (4), the sealing gasket (4) is configured for preventing smoke oil from leaking along a gap between the oil cup assembly (3) and the connecting assembly (1);
   wherein the connecting assembly (1) comprises a connecting base (11) for detachably connecting the oil cup assembly (3) and the battery assembly respectively, and a lower electrode (12) for electrically connecting with the battery assembly;
   wherein the oil cup assembly (3) comprises an oil storage sleeve (31), a vent pipe (32), and a mounting sleeve (34); the vent pipe (32) is located in the oil storage sleeve (31) for discharging smoke produced by an atomization of the atomizing core (2), the mounting sleeve (34) is configured for accommodating the atomizing core (2); the oil storage sleeve (31), the vent pipe (32) and the mounting sleeve (34) enclose an oil storage chamber (33) for storing the smoke oil; the connecting base (11) is abutted against or connected to the oil storage sleeve (31) with interference fit, and the connecting base (11) is provided on an oil filler of the oil storage sleeve (31); one end of the mounting sleeve (34) is fixedly connected to the vent pipe (32), and the other end of the mounting sleeve (34) is detachably connected to the connecting base (11) by a thread or snap structure, the mounting sleeve (34) is provided with a first oil guide hole (341) communicating with the oil storage chamber (33);
   wherein the atomizing core (2) comprises an atomizing sleeve (21), a heating wire assembly (22), a smoke oil retention member (23) and an inner electrode (24), and the smoke oil retention member (23) is made of oil absorbing materials, the heating wire assembly (22) is electrically connected to the inner electrode (24), the smoke oil retention member (23) and the heating wire assembly (22) are accommodated in the atomizing sleeve (21), and the atomizing sleeve (21) is provided with a second oil guide hole (211) communicated with the first oil guide hole (341) for smoke oil in the oil storage chamber (33) to flow into the atomizing core (2);
   wherein the smoke oil retention member (23) is inserted into the atomizing sleeve (21) and is fitted to an inner peripheral surface of the atomizing sleeve (21); the smoke oil retention member (23) is made of a nonwoven fabric or an oil storage sheet, and the smoke oil retention member (23) is configured for storing smoke oil passing through the first oil guide hole (341) and the second oil guide hole (211) to flow into the atomizing core (2), and supplying the smoke oil to the heating wire assembly (22) for an atomization; and
   wherein the inner electrode (24) is located at one end of the atomizing sleeve (21), the inner electrode (24) is abutted against and electrically connected to the lower electrode (12); the atomizing core (2) is slidably sleeved in the mounting sleeve (34) so as to remove the atomizing core (2) after disassembling the connecting assembly (1).

2. The atomizing assembly according to claim 1, wherein the lower electrode (12) and the vent pipe (32) clamp two ends of the atomizing core (2) to fix the atomizing core (2).

3. The atomizing assembly according to claim 1, wherein the sealing gasket (4) is located between the oil cup assembly (3) and the connecting assembly (1), and the sealing gasket (4) is provided with an annular sealing groove (41), the oil storage sleeve (31) is inserted in the sealing groove (41).

4. The atomizing assembly according to claim 1, wherein a limit protrusion (111) for restricting the sealing gasket (4) is formed along a circumferential direction of the connecting base (11); the sealing gasket (4) is defined outside the mounting sleeve (34) and an outer wall surface of the sealing gasket (4) is abutted against the limit protrusion (111) so that the sealing gasket (4) seals and covers on the oil filler of the oil storage sleeve (31).

5. The atomizing assembly according to claim 1, wherein the first oil guide hole (341) serving as an oil guide passage is provided on a side wall of the mounting sleeve (34).

6. The atomizing assembly according to claim 1, wherein the connecting base (11) has a connecting through hole (112) extending through the connecting base (11), one end of the connecting through hole (112) is provided with a first connecting sleeve (113), the end is near the vent pipe (32), the mounting sleeve (34) is provided with a threaded structure which mates with the first connecting sleeve (113), the lower electrode (12) is inserted in the connecting through hole (112).

7. The atomizing assembly according to claim 6, wherein an outer wall surface of the first connecting sleeve (113) is in interference with an inner wall surface of the connecting through hole (112).

8. The atomizing assembly according to claim 1, wherein the heating wire assembly (22) comprises an oil guide (221) connected to the smoke oil retention member (23) and a heating wire (222), the heating wire (222) is wound around the oil guide (221), the oil guide (221) is configured for transferring the smoke oil obtained from the smoke oil retention member (23) to the heating wire (222) for heating and atomizing.

9. The atomizing assembly according to claim 8, wherein the heating wire assembly (22) further comprises a fiberglass tube (223) inserted in the smoke oil retention member (23), the fiberglass tube (223) is provided with a mounting hole (224) through which the oil guide (221) passes, the heating wire (222) is wound around the oil guide (221) located in the fiberglass tube (223).

10. The atomizing assembly according to claim 1, wherein the atomizing assembly further comprises a suction nozzle assembly (5) detachably connected to the oil cup assembly (3), the suction nozzle assembly (5) having a smoke passage (51) extending through the suction nozzle assembly (5), the smoke passage (51) is communicated with the vent pipe (32) for smoke obtained from the atomization to pass through.

11. The atomizing assembly according to claim 10, wherein the suction nozzle assembly (5) comprises a suction nozzle (52) for sucking smoke by users, a suction nozzle connection sleeve (53) and a second connection sleeve (54), one end of the suction nozzle connection sleeve (53) is detachably connected to or integrally formed with the suction nozzle (52), and the other end of the suction nozzle connection sleeve (53) is detachably connected to or integrally formed with the second connection sleeve (54).

12. The atomizing assembly according to claim 11, wherein the suction nozzle connection sleeve (53) is detachably connected to the second connection sleeve (54), an end surface of the suction nozzle connection sleeve (53) extending outwardly to form an inner sleeve (531), the end surface is close to the oil cup assembly (3), one end of the second connection sleeve (54) is inserted into the inner sleeve (531), and the other end of the second connection sleeve (54) is detachably connected to the oil storage sleeve (31).

13. The atomizing assembly according to claim 12, wherein the atomizing assembly further comprises a sealing ring (6) for preventing smoke oil from flowing out of the oil storage chamber (33) along a gap between the connecting assembly (1) and the oil cup assembly (3).

14. The atomizing assembly according to claim 13, wherein the end surface of the suction nozzle connecting sleeve (53) is also provided with an outer sleeve pipe (532) which is sheathed outside the inner sleeve (531); the sealing ring (6) is interposed between the inner sleeve (531) and the outer sleeve pipe (532), and an end surface of the oil storage sleeve (31) is abutted against the sealing ring (6).

15. The atomizing assembly according to claim 11, wherein the suction nozzle connection sleeve (53) is detachably connected to the suction nozzle (52), an end surface of the suction nozzle connection sleeve (53) extending outwardly to form a nozzle fixed sleeve (533), the end surface is close to the suction nozzle (52), the suction nozzle (52) is inserted into the nozzle fixed sleeve (533).

16. The atomizing assembly according to claim 1, wherein the atomizing core (2) further comprises an atomizing cap (25) defined at one end of the atomizing sleeve (21), the end is opposite to the inner electrode (24), the atomizing cap (25) is provided with an atomizing cap through hole (251) penetrating through the atomizing cap (25), and the atomizing cap through hole (251) is communicated with the vent pipe (32).

17. The atomizing assembly according to claim 1, wherein the connecting base (11) and the atomizing sleeve (21) are made of a conductive material or a conductive layer is defined on a surface of the connecting base (11) and the atomizing sleeve (21), when the battery assembly supplies power to the atomizing assembly, the connecting base (11) is electrically connected to the battery assembly and the atomizing sleeve (21), respectively, the lower electrode (12) is electrically connected to the battery assembly and the inner electrode (24), respectively; and
wherein a first insulation sleeve (13) is defined between the connecting base (11) and the lower electrode (12), the first insulation sleeve (13) electrically isolates the connecting base (11) from the lower electrode (12); a second insulation sleeve (26) is defined between the atomizing sleeve (21) and the inner electrode (24), and the second insulation sleeve (26) is configured for making the atomizing sleeve (21) be electrically isolated from the inner electrode (24).

18. The atomizing assembly according to claim 1, wherein an end surface of the inner electrode (24) is provided with a magnetic member (241) magnetically connected to the connecting assembly (1) so as to suck out the atomizing core (2) when the connecting assembly (1) is removed; the end surface is abutted against the lower electrode (12).

19. The atomizing assembly according to claim 1, wherein the atomizing core (2) further comprises an atomizing cap (25) and an elastic member (27); the atomizing cap (25) is provided at one end of the atomizing sleeve (21), the end is opposite to the inner electrode (24); the elastic member (27) is defined between the vent pipe (32) and the atomizing cap (25), the atomizing core (2) is resiliently abutted against the vent pipe (32) through the elastic member (27).

20. An electronic cigarette, wherein the electronic cigarette comprises an atomizing assembly and a battery assembly, wherein the atomizing assembly comprises a connecting assembly (1), an atomizing core (2), an oil cup assembly (3) and a sealing gasket (4), the sealing gasket (4) is configured for preventing smoke oil from leaking along a gap between the oil cup assembly (3) and the connecting assembly (1);
wherein the connecting assembly (1) comprises a connecting base (11) for detachably connecting the oil cup assembly (3) and the battery assembly respectively, and a lower electrode (12) for electrically connecting with the battery assembly;
wherein the oil cup assembly (3) comprises an oil storage sleeve (31), a vent pipe (32), and a mounting sleeve (34); the vent pipe (32) is located in the oil storage sleeve (31) for discharging smoke produced by an atomization of the atomizing core (2), the mounting sleeve (34) is configured for accommodating the atomizing core (2); the oil storage sleeve (31), the vent pipe (32) and the mounting sleeve (34) enclose an oil storage chamber (33) for storing the smoke oil; the connecting base (11) is abutted against or connected to the oil storage sleeve (31) with interference fit, and the connecting base (11) is provided on an oil filler of the oil storage sleeve (31); one end of the mounting sleeve (34) is fixedly connected to the vent pipe (32), and the other end of the mounting sleeve (34) is detachably connected to the connecting base (11) by a thread or snap structure, the mounting sleeve (34) is provided with a first oil guide hole (341) communicating with the oil storage chamber (33);

wherein the atomizing core (2) comprises an atomizing sleeve (21), a heating wire assembly (22), a smoke oil retention member (23) and an inner electrode (24), and the smoke oil retention member (23) is made of oil absorbing materials, the heating wire assembly (22) is electrically connected to the inner electrode (24), the smoke oil retention member (23) and the heating wire assembly (22) are accommodated in the atomizing sleeve (21), and the atomizing sleeve (21) is provided with a second oil guide hole (211) communicated with the first oil guide hole (341) for smoke oil in the oil storage chamber (33) to flow into the atomizing core (2);

wherein the smoke oil retention member (23) is inserted into the atomizing sleeve (21) and is fitted to an inner peripheral surface of the atomizing sleeve (21); the smoke oil retention member (23) is made of a nonwoven fabric or an oil storage sheet, and the smoke oil retention member (23) is configured for storing smoke oil passing through the first oil guide hole (341) and the second oil guide hole (211) to flow into the atomizing core (2), and supplying the smoke oil to the heating wire assembly (22) for an atomization; and wherein the inner electrode (24) is located at one end of the atomizing sleeve (21), the inner electrode (24) is abutted against and electrically connected to the lower electrode (12); the atomizing core (2) is slidably sleeved in the mounting sleeve (34) so as to remove the atomizing core (2) after disassembling the connecting assembly (1).

\* \* \* \* \*

UNITED STATES PATENT AND TRADEMARK OFFICE
CERTIFICATE OF CORRECTION

PATENT NO. : 10,674,766 B2
APPLICATION NO. : 15/508480
DATED : June 9, 2020
INVENTOR(S) : Qiuming Liu Page 1 of 1

It is certified that error appears in the above-identified patent and that said Letters Patent is hereby corrected as shown below:

On the Title Page

In Item (71) Applicant Data, the correct data should be "HUIZHOU KIMREE TECHNOLOGY CO., LTD. SHENZHEN BRANCH, Shenzhen, Guangdong (CN)".

Signed and Sealed this
Eighteenth Day of August, 2020

Andrei Iancu
*Director of the United States Patent and Trademark Office*